United States Patent [19]

Shroot et al.

[11] Patent Number: 4,465,688

[45] Date of Patent: Aug. 14, 1984

[54] 9,10-DIHYDRO-1,8,9-TRIHYDROXY-9,10-ANTHRACENE α,β-ENDOSUCCINIMIDE,α,β-ENDOSUCCINIC ACID AND α,β-ENDOMALEIC ACID AND DERIVATIVE THEREOF

[75] Inventors: Braham Shroot, Antibes; Jean Maignan, Tremblay les Gonesse; Gérard Lang, Epinay-sur-Seine, all of France

[73] Assignee: Groupement d'Interet Economique Centre International de Recherches Dermatologiques C.I.R.D., Valbonne, France

[21] Appl. No.: 393,647

[22] Filed: Jun. 29, 1982

Related U.S. Application Data

[63] Continuation-in-part of Ser. No. 312,640, Oct. 19, 1981.

[30] Foreign Application Priority Data

Oct. 21, 1980 [FR] France .................................. 80 22454

[51] Int. Cl.³ ................ C07D 207/40; C07D 207/404; A61K 31/40
[52] U.S. Cl. .................................. 424/274; 548/419; 560/56; 562/466
[58] Field of Search .......................... 548/419; 424/274

[56] References Cited

U.S. PATENT DOCUMENTS 3,123,618  3/1964  Schumann et al. .................. 548/419
3,678,072  7/1972  Klanderman et al. .............. 548/419

OTHER PUBLICATIONS

The Merk Index, 9th Ed. Merk & Co., Inc. N.J. (1976) p. 452 at 3394.
Schultz et al., Chem. Abstracts 88:104985h (1978).

Primary Examiner—Donald G. Daus
Assistant Examiner—William A. Teoli, Jr.
Attorney, Agent, or Firm—Wegner & Bretschneider

[57] ABSTRACT

The invention concerns adducts of 1,8-dihydroxy-9-anthrone, of formula:

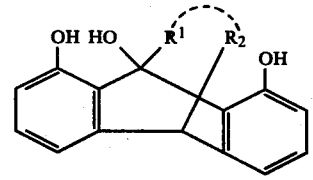

(I)

in which:
$R_1$ and $R_2$, taken together, form one of the following divalent residues:

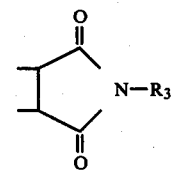

(i)

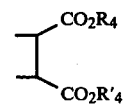

(ii)

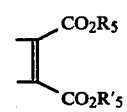

(iii)

$R_3$, $R_4$, $R'_4$, $R_5$ and $R'_5$ representing H, an alkyl group having 1-8 C with the exception of $R_5=R'_5=CH_3$, a monohydroxyalkyl group with 2-8 C, possibly interrupted by one or more oxygens, a cycloalkyl group having 4-6 C, a phenyl group, or a benzyl group.

Utilization of the compounds (I) in human or veterinary medicine, in particular in the treatment of psoriasis and or warts, and in cosmetics.

17 Claims, No Drawings

9,10-DIHYDRO-1,8,9-TRIHYDROXY-9,10-ANTHRACENE α,β-ENDOSUCCINIMIDE,α,β-ENDOSUCCINIC ACID AND α,β-ENDOMALEIC ACID AND DERIVATIVE THEREOF

This application is a continuation-in-part of U.S. Pat. application Ser. No. 312,640, filed Oct. 19, 1981.

The object of the present invention is new chemical compounds which are adducts of 1,8-dihydroxy-9-anthrone, the process of preparing them, and also their utilization in human or veterinary medicine, in particular in the treatment of psoriasis and of warts, and in cosmetics.

The adducts according to the invention can be represented by the following general formula:

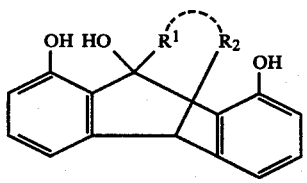  (I)

in which:

$R_1$ and $R_2$, taken together, form one of the following divalent radicals:

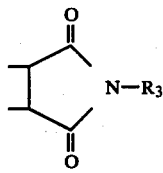  (i)

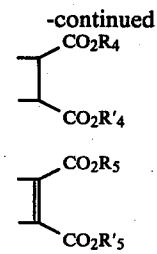

$R_3$, $R_4$, and $R'_4$ represent an atom of hydrogen, a lower alkyl group, straight or branched, with 1–8 carbon atoms; a monohydroxyalkyl group, which maybe interrupted by one or more oxygen atoms and having 2–8 carbon atoms; a cycloalkyl group having 4–6 carbon atoms; a phenyl group; or a benzyl group, and, $R_5$ and $R'_5$, which are the same or different, represent a hydrogen atom, a straight or branched lower alkyl group having 1–8 carbon atoms except for $R_5 = R'_5 = CH_3$; a monohydroxyalkyl group which maybe interrupted by one or more oxygen atoms and having 2–8 carbon atoms; a cycloalkyl group having 4–6 carbon atoms; a phenyl group; or a benzyl group.

According to a variant of the invention, the cycloalkyl, phenyl and benzyl groups can be mono- or poly-substituted with at least one lower alkyl group having 1–4 carbon atoms, a methoxy group, a trifluoromethoxy group, or a halogen (Cl, Br, I or F).

The compounds according to the invention can likewise exist in the form of salts when the groups $R_4$ and/or $R'_4$ or $R_5$ and/or $R'_5$ represent a hydrogen atom.

Among the compounds of formula (I) in which the groups $R_1$ and $R_2$, taken together, from the group (i), there can in particular be cited those collected below in Table I.

TABLE I

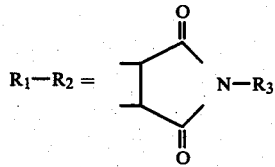

| Compound No. | | $R_3$ |
|---|---|---|
| 1 | 9,10-dihydro-1,8,9-trihydroxy-9,10-anthracene-α,β-endosuccinimide | H |
| 2 | 9,10-dihydro-1,8,9-trihydroxy-9,10-anthracene-α,β-endo-N—methyl succinimide | —$CH_3$ |
| 3 | 9,10-dihydro-1,8,9-trihydroxy-9,10-anthracene-α,β-endo-N—ethyl succinimide | —$C_2H_5$ |
| 4 | 9,10-dihydro-1,8,9-trihydroxy-9,10-anthracene-α,β-endo-N—propyl succinimide | —n $C_3H_7$ |
| 5 | 9,10-dihydro-1,8,9-trihydroxy-9,10-anthracene-α,β-endo-N—isopropyl succinimide | —iso $C_3H_7$ |
| 6 | 9,10-dihydro-1,8,9-trihydroxy-9,10-anthracene-α,β-endo-N—butyl succinimide | —n $C_4H_9$ |
| 7 | 9,10-dihydro-1,8,9-trihydroxy-9,10-anthracene-α,β-endo-N—isobutyl succinimide | —iso $C_4H_9$ |
| 8 | 9,10-dihydro-1,8,9-trihydroxy-9,10-anthracene-α,β-endo-N—hexyl succinimide | —n $C_6H_{13}$ |
| 9 | 9,10-dihydro-1,8,9-trihydroxy-9,10-anthracene-α,β-endo-N—(2-hydroxyethyl) succinimide | —$CH_2$—$CH_2OH$ |
| 10 | 9,10-dihydro-1,8,9-trihydroxy-9,10-anthracene-α,β-endo-N—(1,2-dihydroxypropyl) succinimide | —$CH_2$—$CH$—$CH_2OH$ <br> \| <br> OH |
| 11 | 9,10-dihydro-1,8,9-trihydroxy-9,10-anthracene- | —$(CH_2)_2$—O—$(CH_2)_2$—O |

TABLE I-continued

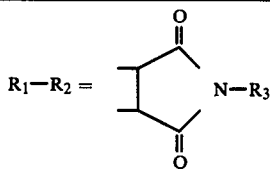

| Compound No. | | $R_3$ |
|---|---|---|
| | α,β-endo-N—(2-hydroxy-2-ethoxyethyl) succinimide | |
| 12 | 9,10-dihydro-1,8,9-trihydroxy-9,10-anthracene-α,β-endo-N—phenyl succinimide | —$C_6H_5$ |

Among the compounds of formula (I) in which the groups $R_1$ and $R_2$, taken together, form the group (ii), there can be cited in particular those collected below in Table II:

Among the compounds of formula (I) in which the groups $R_1$ and $R_2$, taken together, form the group (iii) there can in particular be cited those collected below in Table III:

TABLE II

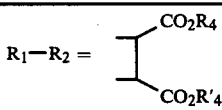

| Compound No. | | $R_4$ | $R'_4$ |
|---|---|---|---|
| 13 | 9,10-dihydro-1,8,9-trihydroxy-9,10-anthracene-α,β-endo-succinic acid | H | H |
| 14 | Methyl 9,10-dihydro-1,8,9-trihydroxy-9,10-anthracene-α,β-endo-succinate | —$CH_3$ | —$CH_3$ |
| 15 | Diethyl 9,10-dihydro-1,8,9-trihydoxy-9,10-anthracene-α,β-endo-succinate | —$C_2H_5$ | —$C_2H_5$ |
| 16 | Dipropyl 9,10-dihydro-1,8,9-trihydroxy-9,10-anthracene-α,β-endo-succinate | —$C_3H_7$ | —$C_3H_7$ |
| 17 | Diisopropyl 9,10-dihydro-1,8,9-trihydroxy-9,10-anthracene-α,β-endo-succinate | —$CH(CH_3)_2$ | —$CH(CH_3)_2$ |
| 18 | Dibutyl 9,10-dihydro-1,8,9-trihydroxy-9,10-anthracene-α,β-endo-succinate | —$C_4H_9$ | —$C_4H_9$ |
| 19 | Diisobutyl-9,10-dihydro-1,8,9-trihydroxy-9,10-anthracene-α,β-endo-succinate | —iso $C_4H_9$ | —iso $C_4H_9$ |
| 20 | Dipentyl 9,10-dihydro-1,8,9-trihydroxy-9,10-anthracene-α,β-endo-succinate | —$C_5H_{11}$ | —$C_5H_{11}$ |
| 21 | Dicyclohexyl 9,10-dihydro-1,8,9-trihydroxy-9,10-anthracene-α,β-endo-succinate | —$C_6H_{11}$ | —$C_6H_{11}$ |

TABLE III

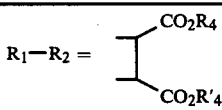

| Compound No. | | $R_5$ | $R'_5$ |
|---|---|---|---|
| 22 | 9,10-dihydro-1,8,9-trihydroxy-9,10-anthracene-α,β-endo-maleic acid | H | H |
| 23 | Monomethyl 9,10-dihydro-1,8,9-trihydrox-9,10-anthracene-α,β-endo-maleate | H | $CH_3$ |
| 24 | Diethyl 9,10-dihydro-1,8,9-trihydroxy-9,10-anthracene-α,β-endo-maleate | —$C_2H_5$ | —$C_2H_5$ |
| 25 | Dipropyl 9,10-dihydro-1,8,9-trihydroxy-9,10-anthracene-α,β-endo-maleate | —$C_3H_7$ | —$CH_3H_7$ |
| 26 | Diisopropyl 9,10-dihydro-1,8,9-trihydroxy-9,10-anthracene-α,β-endo-maleate | —iso $C_3H_7$ | —iso $C_3H_7$ |
| 27 | Dibutyl 9,10-dihydro-1,8,9-trihydroxy-9,10-anthracene-α,β-endo-maleate | —$C_4H_9$ | —$C_4H_9$ |
| 28 | Diisobutyl 9,10-dihydro-1,8,9-trihydroxy-9,10-anthracene-α,β-endo-maleate | —iso $C_4H_9$ | —iso $C_4H_9$ |
| 29 | Dipentyl 9,10-dihydro-1,8,9-trihydroxy-9,10-anthracene-α,β-endo-maleate | —$C_5H_{11}$ | —$C_5H_{11}$ |
| 30 | Dihexyl 9,10-dihydro-1,8,9-trihydroxy-9,10-anthracene-α,β-endo-maleate | —$C_6H_{13}$ | —$C_6H_{13}$ |
| 31 | Dicyclobutyl 9,10-dihydro-1,8,9-trihydroxy-9,10-anthracene-α,β-endo-maleate | —$C_4H_7$ | —$C_4H_7$ |
| 32 | Dicyclopentyl 9,10-dihydro-1,8,9-trihydroxy-9,10-anthracene-α,β-endo-maleate | —$C_5H_9$ | —$C_5H_9$ |

TABLE III-continued

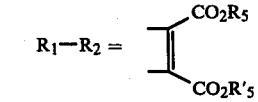

| Compound No. | | $R_5$ | $R'_5$ |
|---|---|---|---|
| 33 | Dicyclohexyl 9,10-dihydro-1,8,9-trihydroxy-9,10-anthracene-α,β-endo-maleate | —$C_6H_{11}$ | —$C_6H_{11}$ |
| 34 | Dibenzyl 9,10-dihydro-1,8,9-trihydroxy-9,10-anthracene-α,β-endo-maleate | —$CH_2C_6H_5$ | —$CH_2C_6H_5$ |
| 35 | Methyl, pentyl 9,10-dihydro-1,8,9-trihydroxy-9,10-anthracene-α,β-endo-maleate | —$CH_3$ | —$C_5H_{11}$ |
| 36 | Methyl, hexyl 9,10-dihydro-1,8,9-trihydroxy-9,10-anthracene-α,β-endo-maleate | —$CH_3$ | —$C_6H_{13}$ |
| 37 | Methyl, octyl 9,10-dihydro-1,8,9-trihydroxy-9,10-anthracene-α,β-endo-maleate | —$CH_3$ | —$C_8H_{17}$ |
| 38 | Ethyl, butyl 9,10-dihydro-1,8,9,-trihydroxy-9,10-anthracene-α,β-endo-maleate | —$C_2H_5$ | —$C_4H_9$ |
| 39 | Ethyl, pentyl 9,10-dihydro-1,8,9-trihydroxy-9,10-anthracene-α,β-endo-maleate | —$C_2H_5$ | —$C_5H_{11}$ |
| 40 | Ethyl, hexyl 9,10-dihydro-1,8,9-trihydroxy-9,10-anthracene-α,β-endo-maleate | —$C_2H_5$ | —$C_6H_{13}$ |

The compounds according to the invention are obtained by reacting 1,8-dihydroxy-9-anthrone (or anthralin) with an unsaturated compound (philodiene), where this compound can be ethylenic or acetylenic, the reaction being carried out in an appropriate organic solvent and in particular in tetrahydrofuran (THF) or acetonitrile, possibly in the presence of a catalyst.

The reaction can be carried out either at ambient temperature or at the boiling point of the solvent utilized, and preferably under an atmosphere of argon and protected from atmospheric moisture and from light.

The course of the reaction is followed by silica gel thin layer chromatography.

After the end of the reaction, and when the expected product crystallizes within the reaction mixture, the product is drained, washed, dried, and then analyzed.

When the product is not obtained in a crystalline form, the reaction solvent is removed under reduced pressure and the residue obtained is then fractionated by passage through a silica gel chromatography column.

The synthesis of the compounds of formula (I) in which the groups $R_1$ and $R_2$, taken together, from the group (i), i.e., the compounds of formula (3), can be represented by the following reaction scheme:

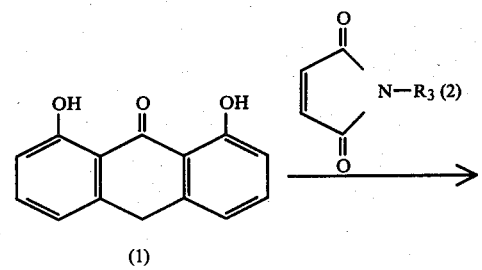

-continued

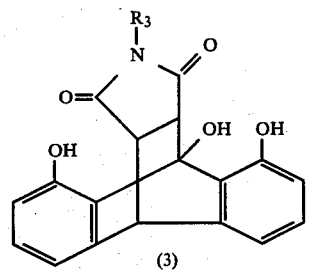

In this synthesis, a 'philodiene' unsaturated compound, namely, the maleamide (2) with $R_3$ = H or a N-substituted maleamide (2) with $R_3 \neq$ H, is reacted in an equimolecular amount or in a slight excess, with anthralin (1) in an organic solvent and preferably in acetonitrile.

As previously indicated for the general conditions, the reaction between anthralin and the N-substituted maleamide or unsubstituted maleamide is effected either at ambient temperature or at the boiling point of the acetonitrile.

When the reaction is carried out at the boiling point of the solvent, the reaction time is generally between 5 and 20 hours.

When the reaction is carried out at ambient temperature, its duration can be of the order of 24 hours to a week.

The synthesis of the compounds of formula I in which $R_1$ and $R_2$, taken together, form the group (iii), i.e., the compounds of formula (5), can be represented by the following reaction scheme:

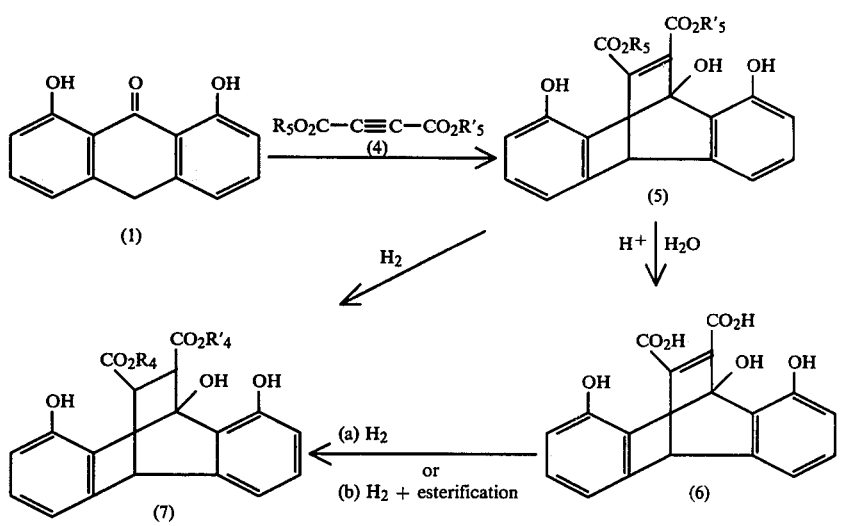

$R_4 = R'_4 = H$ or
$R_4 = R_5$ and $R'_4 = R'_5$

The reaction consists of reacting anthralin (1) with an acetylenic dicarboxylate of formula (4) in THF as organic solvent, in the presence of a basic catalyst such as, for example, lithium methylate.

(Then acetylenic dicarboxylates (4) are prepared by the procedure described by G. J. JEFFREY and A. I. VOGEL, J. Chem. Soc., 1948, p. 674).

The reaction is preferably carried out at ambient temperature for a time which may be between 15 hours and a week.

This reaction is more particularly utilized to prepare compounds of formula (5) in which $R_5 = R'_5$.

When it is desired to obtain compounds of formula (5) in which $R_5 \neq R'_5$, they are preferably obtained by transesterification, starting from compounds of formula (5) in which $R_5 = R'_5$, in the presence of the substitution alcohol as solvent, and in acid catalysis.

Gentle hydrolysis of compounds of formula (5) enables compounds to be otained in which either $R_5$ or $R'_5$ represents a hydrogen atom.

The di-acid of formula (6) is obtained from compounds of formula (5) by treating them, in solution in dioxan, with hydrochloric acid.

After the end of the reaction, the reaction mixture is extracted with chloroform. After drying and evaporation of the chloroform, the residue is then taken up in an appropriate solvent and the product is obtained in the form of crystals.

The compounds of formula (I) in which the groups $R_1$ and $R_2$, taken together, form the group (ii), i.e., the compounds of formula (7), are obtained by catalytic hydrogenation (palladium on carbon) or compounds of formula (5) in solution in an alcohol such as ethanol.

These compounds can likewise be obtained from compounds of formula (6) either directly by hydrogenation when $R_4 = R'_4 = H$ or by hydrogenation followed by esterification of the compound obtained, when $R_4$ and $R'_4 \neq H$.

The structure of the compounds according to the invention could be verified by nuclear magnetic resonance (NMR) spectrography.

The object of the present invention is likewise the utilization of the compounds systemically, and in particular percutaneously, according to the invention, in human or veterinary medicine, in particular in the treatment of psoriasis and warts, and in cosmetics.

Cutaneous psoriasis is essentially manifested by the appearance of dry, whitish or nacreous scales.

Psoriasis preferentially appears on the knees and elbows, sacrum, soles of the feet, palms of the hands, chest and face, and liekwise on hairy hide.

Trials carried out showed that these compounds had good activity when they were incorporated in various pharmaceutical vehicles.

Several examples will now be given, by way of illustration and without any limitative character, of the preparation of the compounds according to the invention.

EXAMPLE 1

9,10-dihydro-1,8,9-trihydroxy-9,10-anthracene-$\alpha,\beta$-endo-succinimide (Compound No. 1)

A mixture of 1.12 g of anthralin ($5 \times 10^{-3}$ mol) and 0.48 g of maleimide ($5 \times 10^{-3}$ mol) in 40 ml of acetonitrile, under an inert atmosphere and protected from atmospheric moisture and from light, is refluxed for 15 hours.

The expected product crystallizes as it is formed. At the end of the reaction, the pale yellow solid is drained and then dried. 1.3 g of product are obtained, decomposing above 220° C.

Analysis: $C_{18}H_{13}NO_5$

Calc. C: 66.87, H: 4.05, N: 4.33, O: 24.74,

Found: 66.76, 4.08, 4.49, 24.90.

EXAMPLE 2

9,10-dihydro-1,8,9-trihydroxy-9,10-anthracene-$\alpha,\beta$-endo-N-ethyl succinimide (Compound No. 3)

A mixture of 2.26 g of anthralin ($10^{-2}$ mol) and an equivalent of N-ethylmaleimide in 50 ml of anhydrous acetonitrile is agitated at ambient temperature under an argon atmosphere, protected from light and from atmospheric moisture, for a week. The product formed crystallizes as it is formed. It is drained, dried under reduced pressure at 115°. There are thus obtained 3.2 g of white powder, decomposing near 220°.

Analysis: $C_{20}H_{17}NO_5$,
Calc. C: 68.37, H: 4.88, N: 3.99, O: 22.77,
Found: 68.22, 4.91, 3.94, 22.85.

EXAMPLE 3

9,10-dihydro-1,8,9-trihydroxy-9,10-anthracene-α,β-endo-N-phenyl succinimide (Compound No. 12)

A mixture of 2.26 g of anthralin and 1.73 g of N-phenyl maleimide (one equivalent) in 100 ml of anhydrous acetonitrile is agitated for 24 hours at ambient temperature, under an argon atmosphere and protected from light. The reaction product crystallizes within the reaction medium. It is drained, then dried under reduced pressure at 100° C.

The white solid thus obtained (3 g) decomposes at 220° C.

Analysis: $C_{24}H_{17}NO_5$,
Calc. C: 72.17, H: 4.29, N: 3.51, O: 20.03,
Found: 72.07, 4.18, 3.44, 19.97.

EXAMPLE 4

9,10-dihydro-1,8,9-trihydroxy-9,10-anthracene-α,β-endo-succinic dimethyl ester (Compound No. 14)

(a) To a solution of 3 g of dimethyl 9,10-dihydro-1,8,9-trihydroxy-9,10-anthracene-α,β-endo-maleate in 60 ml of absolute ethanol placed in an autoclave, there are added 300 mg of palladium fixed on carbon, after carefully washing it with ethanol. A stream of nitrogen is passed through the mixture thus obtained. Hydrogen is then introduced and kept at a pressure of about 90 bars for seven hours.

A stream of nitrogen is then again passed into the solution; the reaction mixture is then filtered. The filtrate is concentrated under reduced pressure at 40° C. After drying, there are thus obtained 3 g of yellow product, contaminated with two impurities.

This product is dissolved in 60 ml of chloroform and the solution is rapidly filtered. A few minutes afterwards, the product crystallizes; it is drained, then dried at ambient temperature.

In order to eliminate the chloroform bound to the product, it is again dissolved in the minimum of acetone (15 ml), and the solution obtained is filtered. To the filtrate is added three times its volume of distilled water. The expected diester crystallizes in the form of white needles. It is drained, washed with water, then dried under reduced pressure over phosphorus pentoxide. (Wt. obtained: 1.5 g). M.P. 126° C.

Analysis: $C_{20}H_{18}O_7$, $H_2O$,
Calc.: C: 61.05, H: 5.19, O: 32.95,
Found: 62.12, 5.18, 32.78.

(b) This product can likewise be prepared in the following manner:

A suspension of 1 g of dimethyl 9,10-dihydro-1,8,9-trihydroxy-9,10-anthracene-α,β-endo-maleate in 15 ml of acetic acid, 8 g of freshly prepared zinc amalgam, and 2 ml of water is agitated at ambient temperature. To this there are added dropwise during one hour, 8 ml of concentrated hydrochloric acid. The mixture thus obtained is agitated for 20 hours at ambient temperature.

The amalgam is then removed by filtration; the filtrate is concentrated at reduced pressure at a temperature below 50° C.

The solid obtained is purified by the method as above.

EXAMPLE 5

9,10-dihydro-1,8,9-trihydroxy-9,10-anthracene-α,β-endo-maleic acid (Compound No. 22)

(a) To a solution of 50 g of anthralin in 600 ml of anhydrous THF under an inert atmosphere and protected from light and atmospheric moisture, there are added 15 ml of a 1% methanolic solution of lithium methylate, then 44 ml of methyl acetylenedicarboxylate. The mixture thus obtained is agitated for two days at ambient temperature, then concentrated to a tenth of its volume. 300 ml of anhydrous benzene are then added.

One hour later, the solid is drained, washed with a benzene/hexane mixture, then dried. The 49 g of 9,10-dihydro-1,8,9-trihydroxy-9,10-anthracene-α,β-endo-maleic acid dimethyl ester are recrystallized from toluene. A beige powder is obtained which decomposes at a temperature of around 200° C.

Analysis: $C_{20}H_{16}O_7$
Calc.: C: 65.22, H: 4.38, C: 30.41,
Found: 65.11, 4.37, 30.32.

(b) A solution of 15 g of diester thus obtained in a mixture of 200 ml of dioxan and 300 ml of 5N hydrochloric acid is kept at 100° C. for 24 hours, protected from light and under an argon atmosphere. The reaction mixture is then extracted with chloroform. The chloroform phase is dried over sodium sulfate, then rectified under reduced pressure. The residue obtained is taken up in an ether-hexane mixture; the expected product crystallizes slowly. It is drained and dried at 110° C. under reduced pressure. There are thus obtained 12 g of beige powder which are dissolved in 75 ml of acetone; the solution is filtered. 300 ml of benzene are then added to the filtrate. The diacid crystallizes; traces of diester are thus eliminated. It is then agitated in the minimum of 2N hydrochloric acid, drained, then dried at 110° C. under reduced pressure and over phosphorus pentoxide for 24 hours. The beige solid obtained contains 0.75 mol of water.

Analysis $C_{18}H_{12}O_7$ (3/4 $H_2O$)
Calc. C: 61.11, H: 3.85, O: 35.05,
Found 60.93, 4.26, 34.95.

EXAMPLE 6

Monomethyl 9,10-dihydro-1,8,9-trihydroxy-9,10-anthracene-α,β-endo-maleate (No. 23)

A solution of 15 g of dimethyl 9,10-dihydro-1,8,9-trihydroxy-9,10-anthracene-α,β-endo-maleate in 900 ml of 2N hydrochloric acid and 900 ml of dioxan is kept at 100° C. for 5 hours while protected from light. At this stage, it is verified by thin layer chromatography that little of the starting diester remains and that the diacid (Compound No. 22) has not yet been formed.

The reaction mixture is concentrated under reduced pressure; the solid is washed with water and dried. The 13 g of product thus obtained are recrystallized once from an acetone-toluene mixture and a second time from an acetonemethylene chloride mixture.

There are thus obtained 4.5 g of white powder melting at 315°–320° C. (instantaneous melting). The mass spectrum corresponds to the expected structure ($C_{19}H_{14}O_7$, molecular peak at m/e : 354), and also the NMR spectrum.

EXAMPLE 7

Diethyl 9,10-dihydro-1,8,9-trihydroxy-9,10-anthracene-α,βendo-maleate (Compound No. 24 )

To a suspension of 3.39 g of anthralin ($1.5 \times 10^{-2}$ mol) in 30 ml of anhydrous THF, agitated under an argon atmosphere and protected from light and atmospheric moisture, there are added in succession 1 ml of a 0.5% methanolic solution of lithium methylate, then 4 ml of ethyl acetylenedicarboxylate.

The reaction mixture is then brought to a temperature of 60° C. during three hours, then concentrated under reduced pressure.

The dark red oil obtained is then taken up in 20 ml of anhydrous benzene; on cooling, a yellow solid crystallizes. It is drained, then crystallized a second time from benzene.

The white crystals thus obtained after filtration, then drying at 100° C., have a melting point of 196° C.

Analysis: $C_{22}H_{20}O_7$
Calc. C: 66.66, H: 5.08, O: 28.25
Found: 66.65, 5.11, 28.27.

EXAMPLE 8

Diisopropyl 9,10-dihydro-1,8,9-trihydroxy-9,10-anthracene-α,β-endo-maleate (Compound No. 26)

To a suspension of 11.3 g of anthralin in 150 ml of anhydrous THF, placed under an inert atmosphere and protected from atmospheric moisture and light, there are added 15 g of isopropyl acetylenedicarboxylate, then 4 ml of a 0.5% methanol solution of lithium methylate. The reaction mixture is brought to the boiling point of THF during two hours, then concentrated under reduced pressure. The dark red residue is solubilized in a minimum amount of toluene. The toluene phase is deposited on a silica gel chromatography column.

The expecteed product is eluted with chloroform, then recrystallized from a methylene chloride/hexane mixture after concentration of the elution phases. After draining and drying, there are obtained 10 g of white crystals with melting point 203° C.

Analysis: $C_{24}H_{24}O_7$,
Calc.: C: 67.91, H: 5.70, O: 26.39,
Found: 68.15, 5.90, 26.47.

Example 9

Dibutyl 9,10-dihydro-1,8,9-trihydrox-9,10-anthracene-α,β-endo-maleate (Compound No. 27)

To a suspension of 3.40 g of anthralin in 40 ml of anhydrous THF, placed under an argon atmosphere and protected from atmospheric moisture and light, there are successively added 1 ml of a 0.5% methanolic solution of lithium methylate, then 5 g of freshly distilled butyl acetylenedicarboxylate. The reaction mixture is then brought to the boiling point of THF during two hours. It is then concentrated under reduced pressure. The residual oil obtained is diluted with 30 ml of benzene, and the solution is then deposited directly onto a silica gel column. The expected product is eluted with chloroform. After concentration of the chloroform phases, the solid is crystallized once from cyclohexane and then from a hexane/benzene mixture. The white crystals thus isolated melt at 148° C.

Analysis: $C_{26}H_{28}O_7$,
Calc. C: 69.01, H: 6.24, O: 24.75,
Found: 68.86, 6.26, 24.85.

EXAMPLE 10

Dipentyl 9,10-dihydro-1,8,9-trihydroxy-9,10-anthracene-α,β-endo-maleate (Compound No. 29)

A solution of 5 g of methyl, pentyl 9,10-dihydro-1,8,9-trihydroxy-9,10-anthracene-α,β-endo-maleate (compound No. 35) in 50 ml of pentanol is brought to boiling during 40 hours in the presence of several drops of sulfuric acid. After cooling, the expected product is precipitated by the addition of hexane. There are obtained 3 g of beige powder which is purified by chromatogrphy on silica gel, followed by crystallization from benzene-hexane mixture.

The beige crystals obtained have a melting point of 144° C.

Elementary analysis: $C_{28}H_{32}O_7$,
Calc. C: 69.98, H: 6.71, O: 23.31,
Found: 70.06, 6.72, 23.19.

EXAMPLE 11

Dicyclohexyl 9,10-dihydro-1,8,9-trihydroxy-9,10-anthracene-α,β-endo-maleate (Compound No. 33)

To a suspension of 11.3 g of anthralin in 150 ml of anhydrous tetrahydrofuran, protected from atmospheric moisture and light and placed under an inert atmosphere, there are added 20.38 g of dicyclohexyl acetylenedicarboxylate and then 3.5 ml of a 0.5% methanolic solution of lithium methylate. The reaction mixture is maintained at the boiling point of tetrahydrofuran for one hour. After concentration under reduced pressure, the product obtained is dissolved in a minimum of toluene and deposited on a silica gel chromatogrphy column. The dicyclohexyl 9,10-dihydro-1,8,9-trihydroxy-9,10-anthracene-α,β-endo-maleate is eluted with a 4:1 mixture of toluene/ethyl acetate, then crystallized from a mixture of toluene and hexane and finally washed with methylene chloride. After drying, there are thus obtained 16 g of white crystals with a melting point of 230° C.

Analysis: $C_{30}H_{32}O_7$,
Calc. C: 71.41, H: 6.39,
Found 71.63, 6.48.

EXAMPLE 12

Dibenzyl 9,10-dihydro-1,8,9-trihydroxy-9,10-anthracene-α,β-endo-maleate (Compound No. 34)

To a suspension of 11.3 g of anthralin in 150 ml of anhydrous THF protected from atmospheric moisture and light and placed under an inert atmosphere, there are added 16 g of benzyl acetylenedicarboxylate and 3.5 ml of a 0.5% methanolic solution of lithium methylate. The reaction mixture is agitated for 18 hours at ambient temperature. After concentration under reduced pressure, the highly-colored oil obtained is dissolved in 150 ml of methylene chloride. This solution is washed with 2N hydrochloric acid and then water, and is finally dried over magnesium sulfate. On addition of 400 ml of hexane, there are obtained 19 g of solid, which is purified by passage through a silica gel filter. There are thus obtained 15.2 g of white crystals with a melting point of 192° C.

Analysis: $C_{32}H_{24}O_7$,
Calc. C: 73.84, H: 4.65, O: 21.51,
Found: 73.75, 4.73, 21.71.

EXAMPLE 13

Methyl pentyl 9,10-dihydro-1,8,9-trihydroxy-9,10-anthracene-α,β-endo-maleate (Compound No. 35)

A solution of 15 g of dimethyl 9,10-dihydro-1,8,9-trihydroxy-9,10-anthracene-α,β-endo-maleate in 100 ml of pentanol s brought during 24 hours to a temperature of 130° C. in the presence of several drops of sulfuric acid.

The solution is then concentrated under reduced pressure. The residue obtained is dissolved in toluene; the toluene phase is washed with water, then dried over sodium sulfate. After concentration, it is deposited on a silica gel column. The expected product is eluted with chloroform, then, after concentration of the elution phases, 12.5 of a beige solid are obtained, and are recrystallized from toluene. The crystals are drained, washed under reduced pressure. Their melting point is 136° C.

Analysis: $C_{24}H_{24}O_7$,
Calc. C: 67.91, H: 5.70, O: 26.39,
Found: 67.72, 5.61, 26.38.

EXAMPLE 14

Methyl hexyl 9,10-dihydro-1,8,9-trihydroxy-9,10-anthracene-α,β-endo-maleate (Compound No. 36)

A solution of 12.6 g of dimethyl 9,10-dihydro-1,8,9-trihydroxy-9,10-anthracene-α,β-endo-maleate in 100 ml of hexanol is kept at a temperature of 130° during 72 hours in the presence of several drops of sulfuric acid. The solution is then concentrated under reduced pressure, then taken up again in toluene. The toluene phase is then washed with water, dried over sodium sulfate, and then deposited on a silica gel chromatography column. The expected product is eluted with chloroform.

After concentration of the elution phases, there are obtained 6 g of beige powder, which is crystallized twice from a benzene/hexane (1:2) mixture. The white crystals thus obtained have a melting point of 118° C.

Analysis: $C_{25}H_{26}O_7$,
Calc. C: 68.48, H: 5.98, O: 25.54,
Found: 68.58, 5.94, 25.57.

Regarding the treatment of psoriasis or warts, a composition containing a compound of the present invention is topically administered directly to the affected area. It may, for example, be applied as part of a thickened lotion. A suitable thickening agent for such an application would be petroleum jelly.

An example of an anti-psoriasis composition embodied within the scope of the present invention is as follows:

9,10-dihydro-1,8,9-trihydroxy-9,10-anthracene-α,β-endo-N-ethyl succinimide — 1.5 g,
Salicylic acid — 0.7 g,
Petroleum jelly —100 g.

To the petroleum jelly at 60° C., there is added under stirring the active ingredient and then the salicylic acid. After cooling to ambient temperatures, the suspension obtained is refined by passing it to roller mill.

By applying the suspension once a day during three weeks, excellent results are obtained on the psoriasis areas very similar to those obtained with anthralin but with no primary irritation and without staining of the skin.

We claim:
1. A compound of the formula

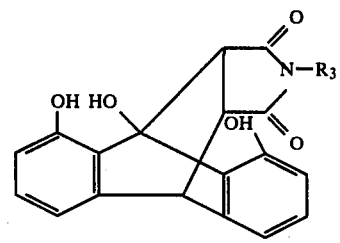

wherein $R_3$ is selected from the group consisting of hydrogen; straight or branched lower alkyl having 1–8 carbon atoms; monohydroxyalkyl having 2–8 carbon atoms, the carbon chain of which may have one oxygen; cycloalkyl having 4–6 carbon atoms; phenyl and benzyl.

2. The compound of claim 1 which is 9,10-dihydro-1,8,9-trihydroxy-9,10-anthracene-alpha,beta-endosuccinimide.

3. A compound according to claim 1 wherein $R_3$ is lower alkyl having 1–8 carbon atoms.

4. The compound of claim 3 which is 9,10-dihydro-1,8,9-trihydroxy-9,10-anthracene-alpha,beta-endo-N-methyl succinimide.

5. The compound of claim 3 which is 9,10-dihydro-1,8,9-trihydroxy-9,10-anthracene-alpha,beta-endo-N-ethyl succinimide.

6. The compound of claim 3 which is 9,10-dihydro-1,8,9-trihydroxy-9,10-anthracene-alpha,beta-endo-N-propyl succinimide.

7. The compound of claim 3 which is 9,10-dihydro-1,8,9-trihydroxy-9,10-anthracene-alpha,beta-endo-N-isopropyl succinimide.

8. The compound of claim 3 which is 9,10-dihydro-1,8,9-trihydroxy-9,10-anthracene-alpha,beta-endo-N-butyl succinimide.

9. The compound of claim 3 which is 9,10-dihydro-1,8,9-trihydroxy-9,10-anthracene-alpha,beta-endo-N-isobutyl succinimide.

10. The compound of claim 3 which is 9,10-dihydro-1,8,9-trihydroxy-9,10-anthracene-alpha,beta-endo-N-hexyl succinimide.

11. A compound according to claim 1 wherein $R_3$ is monohydroxyalkyl having 2–8 carbon atoms, the carbon chain of which may contain one oxygen atom.

12. The compound of claim 11 which is 9,10-dihydro-1,8,9-trihydroxy-9,10-anthracene-alpha,beta-endo-N-(2-hydroxyethyl) succinimide.

13. The compound of claim 11 which is 9,10-dihydro-1,8,9-trihydroxy-9,10-anthracene-alpha,beta-endo-N-(2-hydroxy-2-ethoxyethyl) succinimide.

14. The compound of claim 1 which is 9,10-dihydro-1,8,9-trihydroxy-9,10-anthracene-alpha,beta-endo-N-phenyl succinimide.

15. 9,10-dihydro-1,8,9-trihydroxy-9,10-anthracene-alpha, beta-endo-N-(1,2-dihydroxy propyl) succinimide.

16. A pharmaceutical composition for the treatment of psoriasis or warts comprising an effective amount of a compound of claim 1 in a suitable carrier for topical administration.

17. A method for the treatment of psoriasis or warts consisting of applying to the affected area of the skin to be treated an effective amount of the composition of claim 1.

* * * * *